United States Patent
McPherson et al.

(10) Patent No.: US 7,476,101 B2
(45) Date of Patent: Jan. 13, 2009

(54) DENTAL HANDPIECE WITH REMOVABLE APEX FINDING ELECTRODE

(75) Inventors: Roger W. McPherson, Calgary (CA); Richard Tuan Le, Garden Grove, CA (US); Patrick L. Johnson, Cowan Heights, CA (US)

(73) Assignee: Pro-Dex, Inc., Santa Ana, CA (US)

( * ) Notice: Subject to any disclaimer, the term of this patent is extended or adjusted under 35 U.S.C. 154(b) by 0 days.

(21) Appl. No.: 11/383,155

(22) Filed: May 12, 2006

(65) Prior Publication Data

US 2006/0257818 A1    Nov. 16, 2006

Related U.S. Application Data

(60) Provisional application No. 60/680,234, filed on May 12, 2005.

(51) Int. Cl.
*A61C 3/00*    (2006.01)
(52) U.S. Cl. .............................. 433/75; 433/27; 600/590
(58) Field of Classification Search .................. 433/32, 433/75, 102, 114, 116, 126, 27, 224; 600/590
See application file for complete search history.

(56) References Cited

U.S. PATENT DOCUMENTS

| | | | |
|---|---|---|---|
| 3,449,831 A * | 6/1969 | Vandis | ........................ 433/100 |
| 4,243,388 A | 1/1981 | Arai | |
| 5,096,419 A | 3/1992 | Kobayashi et al. | |
| 5,211,556 A | 5/1993 | Kobayashi et al. | |
| 5,295,833 A | 3/1994 | Chihiro et al. | |
| 5,897,315 A * | 4/1999 | Nakayama et al. | ............. 433/72 |
| 5,902,105 A | 5/1999 | Uejima et al. | |
| 5,980,248 A | 11/1999 | Kusakabe et al. | |
| 6,520,773 B1 | 2/2003 | Weber | |
| 7,070,411 B2 * | 7/2006 | Nakanishi et al. | ............. 433/72 |

FOREIGN PATENT DOCUMENTS

| | | |
|---|---|---|
| DE | 274169 A1 | 12/1989 |
| JP | 04064354 | 2/1992 |
| JP | 04073055 | 3/1992 |
| JP | 04348749 | 12/1992 |
| JP | 05064643 | 3/1993 |
| JP | 05092014 | 4/1993 |
| JP | 06181937 | 7/1994 |

(Continued)

OTHER PUBLICATIONS

Denta Port ZX Manual; J. Morita Mfg. Corp; Mar. 12, 2003.

(Continued)

*Primary Examiner*—John J Wilson
*Assistant Examiner*—Heidi M Bashaw
(74) *Attorney, Agent, or Firm*—Knobbe, Martens, Olson & Bear, LLP

(57) ABSTRACT

A dental handpiece is provided with a collar that moves along an outer surface of the handpiece. A contact is secured to the collar. The collar interfaces with an electrical circuit that extends within the dental handpiece. The contact is removable from the collar and the contact defines an electrical connection between a cutting tool used with the dental handpiece and the electrical circuit that extends within the dental handpiece.

20 Claims, 9 Drawing Sheets

FOREIGN PATENT DOCUMENTS

| | | |
|---|---|---|
| JP | 08038510 | 2/1996 |
| JP | 09224961 A | 9/1997 |

OTHER PUBLICATIONS

Micro Motors Low Speed Electric Motor; Dyna Torq; 2 pages.

Tri Auto ZX; A Cordless Endodontic Treatment Handpiece Manual; 18 pages.

Tri Auto ZX, The Dental Advisor; J. Morita USA, Inc.; Oct. 18, 2004; 2 pages; website: http://jmoritausa.com/tri_auto_zx.asp.

J. Morita USA Inc.; Crown & Bridge Removers; Oct. 18, 2004; website: http://www.jmoritausa.com/crown_%20bridge_removers_page.asp.

J.Morita USA Inc.; Curing Lights; Jetlite 4000 Plus; Oct. 18, 2004; website: http://www.jmoritausa.com/curing_lights_page.asp.

J. Morita USA Inc.; ATD Automatic Crown & Bridge Remover; Oct. 18, 2004; website: http://www.jmoritausa.com/atd_automatic_crown_bridge_remover.asp.

J. Morita USA INc.; Jetlite 4000 Plus; Oct. 18, 2004; website: http://www.jmoritausa.com/jetlite_4000_plus.asp.

J. Morita USA Inc.; Endodonitcs; Oct. 18, 2004; website: http://www.jmoritausa.com/endodontics_page.asp.

J. Morita USA Inc.; Dentaport ZX; Oct. 18, 2004; website: http://www.jmoritausa.com/dentaport.asp.

J. Morita USA Inc.; Root ZX Oct. 18, 2004; website: http://www.jmoritausa.com/root_zx.asp.

J. Morita USA Inc.; Rotary Master; Oct. 18, 2004; website: http://www.jmoritausa.com/rotary_master.asp.

* cited by examiner

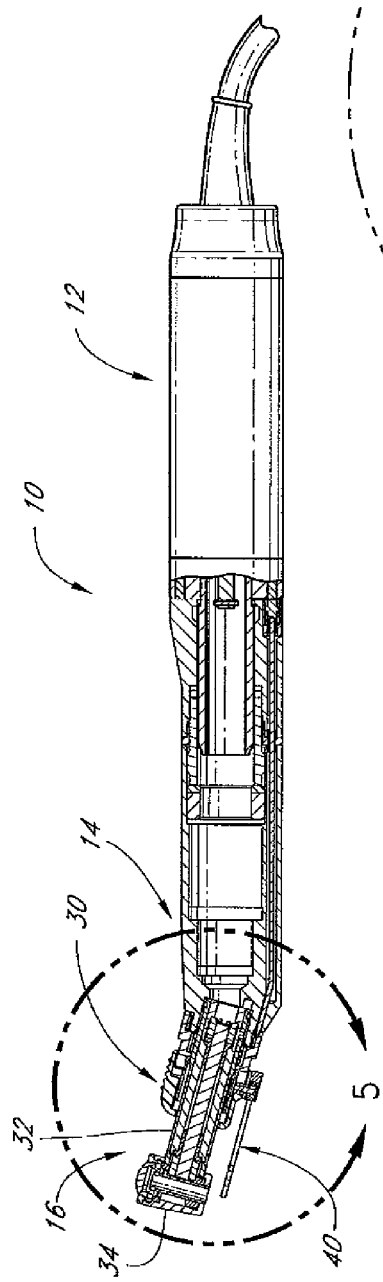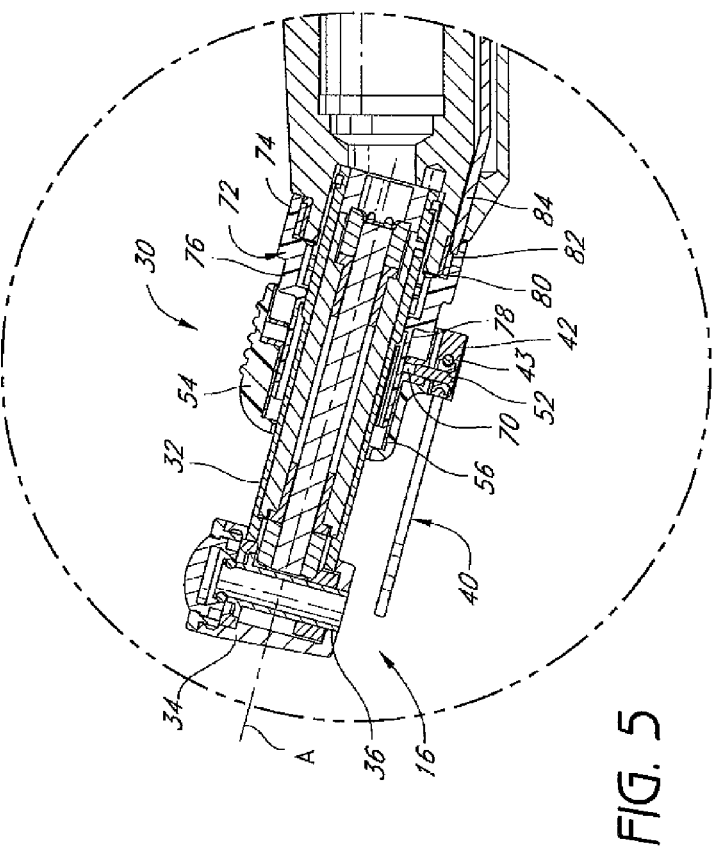
FIG. 4
FIG. 5

DENTAL HANDPIECE WITH REMOVABLE APEX FINDING ELECTRODE

RELATED APPLICATIONS

This application claims the priority benefit of 35 U.S.C. § 119(e) of U.S. Provisional Patent Application No. 60/680,234, filed on May 12, 2005, which is hereby incorporated by reference in its entirety.

BACKGROUND OF THE INVENTION

1. Field of the Invention

The present invention generally relates to dental handpieces having root canal apex-finding electrodes. More particularly, the present invention relates to such handpieces that feature movable and removable apex-finding electrodes.

2. Description of the Related Art

For treatment of a root canal during dental operations, a cutting tool, such as a reamer or file can be used to enlarge the root canal. In some configurations, the cutting tool also is used as a signal conductor in a circuit that measures the root canal length. In such configurations, a main control unit is electrically connected to the cutting tool with an electrode such that an electrical signal can be transmitted between the cutting tool and the control unit. The electrode physically contacts the cutting tool.

In some configurations, a circuit or wire is connected to the electrode and the circuit or wire extends outside of the handpiece to a connection to the control unit. Thus, the circuit or wire is external to the handpiece. In such a configuration, the circuit or wire requires manual manipulation to control its location and can get in the way when procedures are performed with the handpiece.

In other configurations, the circuit or wire extends through an internal portion of the handpiece and is removably connected to the electrode such that the electrode can be disconnected from the wire or circuit. In such a configuration, the manner in which the electrode is secured to the wire or circuit provides a limited contact region between the cutting tool and the circuit or wire. The limited contact region can result in inconsistent contact, which can impair performance of the handpiece.

In both configurations described above, sterilization of the dental equipment by autoclaving can be difficult, if not impossible, without removal of the electrode and any external wires or circuits.

SUMMARY OF THE INVENTION

Accordingly, a dental handpiece is desired in which the connecting wire or circuit extends within the handpiece and is connected to the electrode in a manner which does not result in an external connection and which provides an enlarged connection area.

One aspect of the present invention relates to a dental handpiece and collar construction. The dental handpiece comprises a main body, a neck section and a head unit. A cable extends into a proximal end of the main body. A distal end of the main body is connectable to the neck section. The head unit comprises a shank that comprises a longitudinal axis. The collar is positioned around the shank and is moveable along the longitudinal axis. The collar comprises an outer housing and an inner sleeve. The inner sleeve is in electrical communication with a conducting member that extends through the neck section of the dental handpiece. The outer housing comprises a projecting portion. A docking region is defined within the projecting portion. The docking region comprises a pair of side walls. A mounting block is positionable within the docking region. The mounting block comprises a pair of side walls that abut with the side walls of the docking region. A contact is secured to the mounting block such that the contact is positioned external of the head unit. The contact comprises a generally U-shaped configuration. A fastener secures the contact to the inner sleeve such that the inner sleeve is in electrical communication with the contact.

Another aspect of the present invention relates to a dental handpiece and collar construction. A conducting member extends internally through the handpiece. The handpiece comprises a head unit. The head unit comprises a shank. The shank comprises a longitudinal axis and an outer surface. A collar is positioned over the outer surface of the shank and is slideable along the longitudinal axis. A contact is secured to the collar and the contact is positioned vertically below the head unit. The contact is in electrical communication with the conducting member through the collar. The contact abuts a cutting tool positioned in the handpiece when the collar is slid axially along the shank toward the cutting tool.

A further aspect of the present invention relates to a dental handpiece and collar construction comprising a head unit. The head unit comprises a shank and a head housing. The head housing is connected to a main body. The shank extends in a proximal direction from the head housing and comprises a longitudinal axis. A sleeve is positioned within the head housing. The sleeve is adapted to retain a cutting tool for use with the dental handpiece. A collar is positioned about the shank of the head unit and is moveable along the longitudinal axis of the shank. A contact is removably connected to the collar. The contact is adapted to contact the cutting tool when the sleeve is moved along the longitudinal axis in a distal direction. The contact is in electrical communication with an electrical path that extends between the collar and the main body through an internal portion of the head unit.

BRIEF DESCRIPTION OF THE DRAWINGS

These and other features, aspects and advantages of the present invention will now be described with reference to the drawings of a preferred embodiment, which embodiment is intended to illustrate and not to limit the present invention. The figures comprise twelve drawings.

FIG. 4 is a partially sectioned view of the dental handpiece of FIG. 1.

FIG. 5 is an enlarged view of the cross-section taken in FIG. 4 and showing an electrical connection between a contact and an internal circuit of the dental handpiece of FIG. 1.

DETAILED DESCRIPTION OF THE PREFERRED EMBODIMENT

Figure 1:
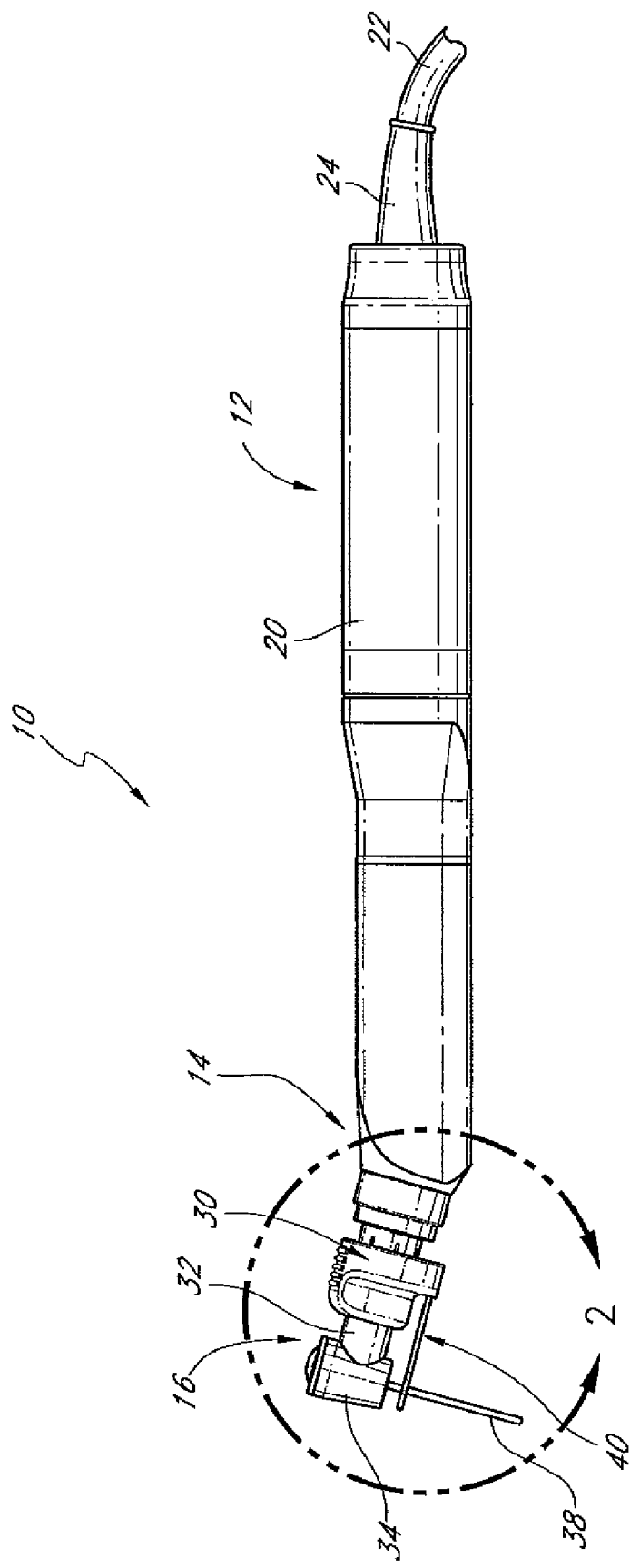
FIG. 1 is a side view of a dental handpiece that is arranged and configured in accordance with certain features, aspects and advantages of the present invention.
Figure 3:
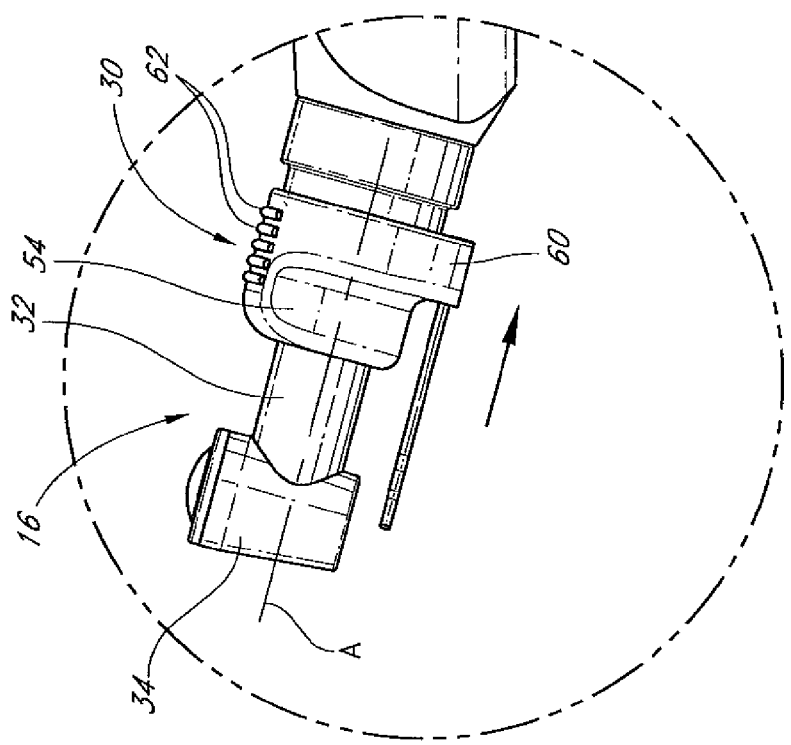
FIG. 3 is similar to the view of FIG. 2, showing the movable contact collar in a second position.

With reference initially to FIG. 1, a dental handpiece 10 that is arranged and configured in accordance with certain features, aspects and advantages of the present invention is shown. The dental handpiece 10 generally comprises a main body 12, a neck section 14, and a head unit 16. The neck section 14 and the head unit 16 can be configured as an integrated unit or can be provided as separate components. When the components 14, 16 are provided separately, the components 14, 16 preferably are joined together in a suitable manner that will house the mechanical and electrical connections described herein or otherwise used to create a functional handpiece. In general, the neck section 14 and the main body 12 are separable to allow sterilization of the neck section 14 and the head unit 16 in manners known to those of ordinary skill in the art. Any suitable coupling can be used.

The illustrated main body 12 comprises a case 20 that defines an inner chamber (not shown). Within the inner chamber, the main body 12 preferably contains a drive motor (not shown). Any suitable drive motor can be used. In the preferred arrangement, the drive motor comprises an electric motor. In some configurations, an air motor or a pneumatic motor can be provided. Any other suitable drive motor also can be used. Rotation of an output shaft of the drive motor is conveyed to a cutting tool using any suitable transmission mechanism.

The case 20 can be sized and configured to provide a suitable gripping area while keeping in mind the desire to encase the drive motor. The gripping area is sized and configured for grasping by the hand of an operator during use of the handpiece 10. While pistol grip style constructions can be used, such constructions provide decreased operator control relative to the illustrated contra angle construction.

The drive motor is supplied with electricity and/or control signals via suitable electrical conductors. In the illustrated arrangement, the electrical conductors are contained with a cable 22. The cable 22 extends into the proximal end of the illustrated main body 12. In the illustrated arrangement, a flexible boot 24 enshrouds the end of the cable 22 and provides protection to the coupling between the cable 22 and the main body 12. While the illustrated embodiment is shown in the context of a handpiece having a cable 22, certain features, aspects and advantages of the present invention may find utility with other types of handpieces, including cordless handpieces, for instance, but without limitation.

With reference now to FIGS. 2-5, the dental handpiece 10 preferably comprises a movable collar 30 that is positioned on the head unit 16. The collar 30 extends around a shank 32 of the head unit 16. While the illustrated collar 30 extends in a full circle, some constructions of the collar 30 may extend less than the full circle. Preferably, however, the illustrated collar extends more than halfway around a full circle.

In some configurations, the shank 32 comprises an axis A or other longitudinal datum line. In other words, the shank 32 need not be generally cylindrical in shape but can have other shapes, as desired. In some embodiments, the axis A may bend or be other than linear. The collar 30, where the shank 32 is not generally cylindrical, preferably has a complementary shape and configuration. The collar 30 preferably is translatable in an axial direction relative to the datum line A. In other words, the illustrated collar 30 defines a slideable member. In some other configurations, the collar 30 may rotate about the axis A rather than slide along the axis A or the collar 30 may slide along and rotate about the axis A.

With reference to FIGS. 4 and 5, the head unit 16 further comprises a head housing 34. The head housing 34 can have any suitable configuration. As best illustrated in FIG. 5, the head housing 34 preferably contains a sleeve 36. The sleeve 36 is mounted for rotation within the head housing 34. The sleeve 36 can be arranged and configured to secure a dental instrument 38, such as the file shown in FIG. 2, for instance but without limitation. The dental instrument 38 can be a cutting tool, such as a reamer, for example. In the illustrated configuration, the dental instrument is one that can be used during root canal procedures and the like.

Figure 6:
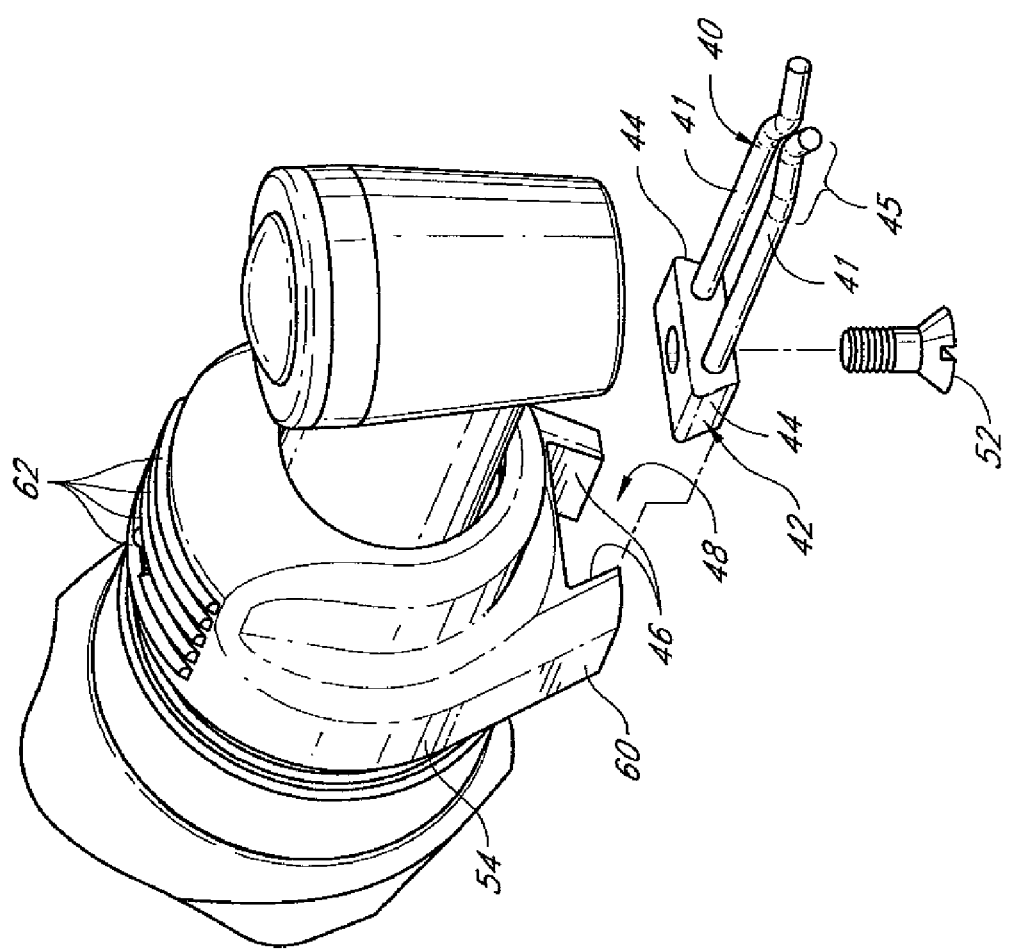
FIG. 6 is an enlarged perspective view of a portion of the dental handpiece of FIG. 1 in which the contact has been removed from the movable contact collar.
Figure 7:
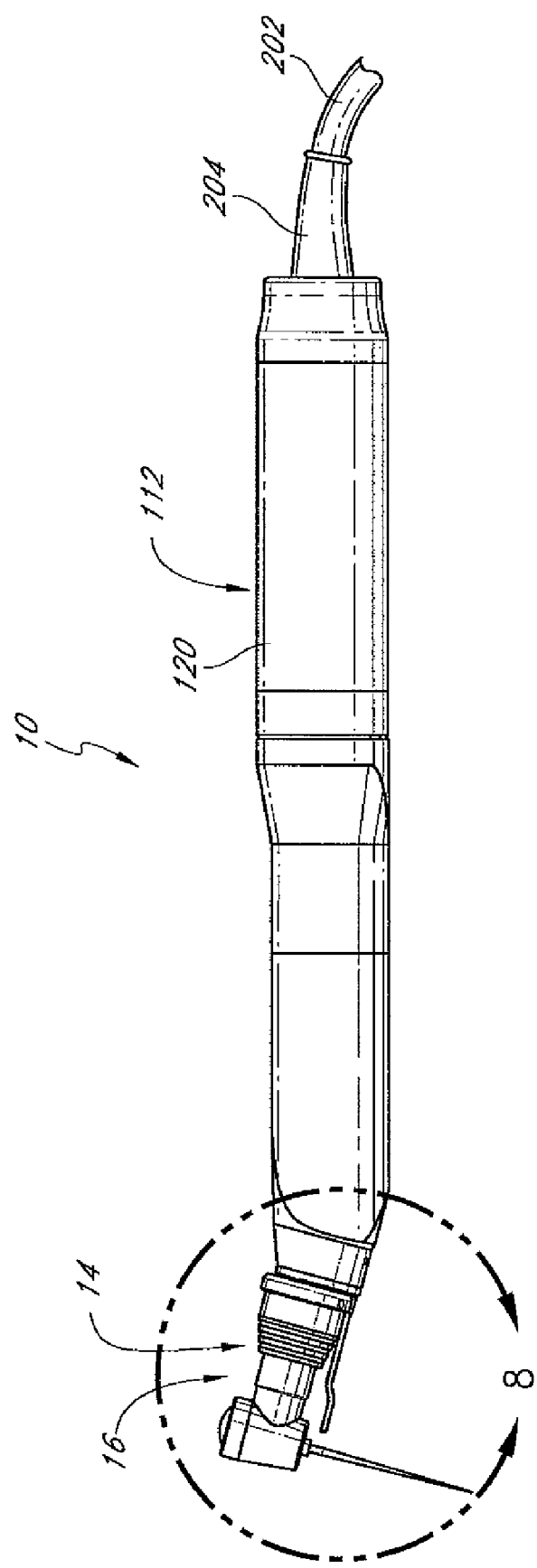
FIG. 7 is a side view of another dental handpiece that is arranged and configured in accordance with certain features, aspects and advantages of the present invention.
Figure 9:
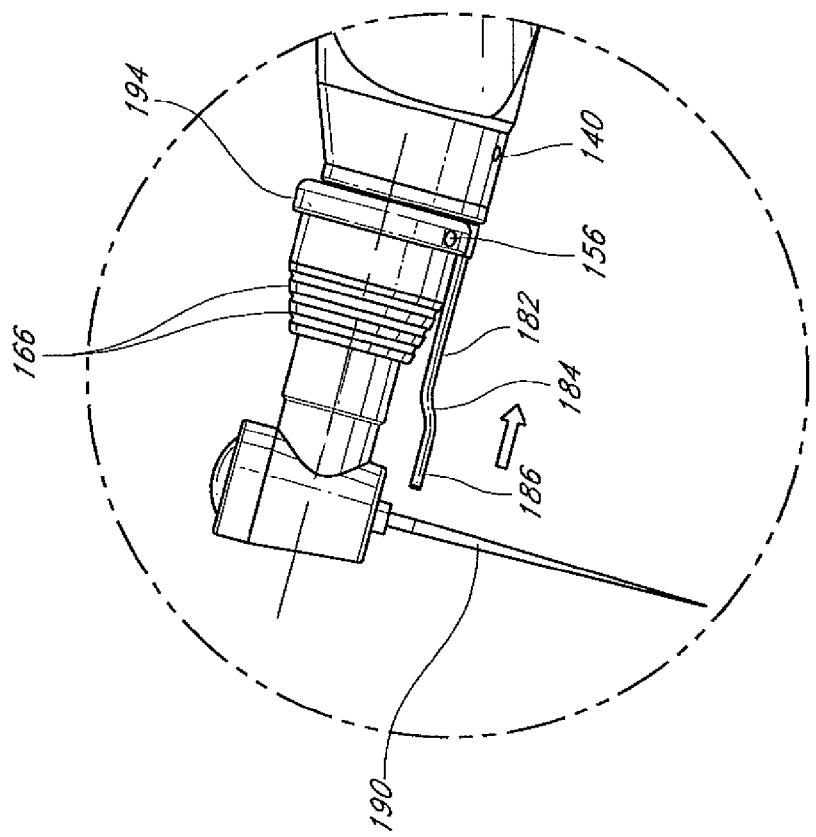
FIG. 9 is similar to the view of FIG. 8, showing the movable contact collar in a second position.
Figure 8:
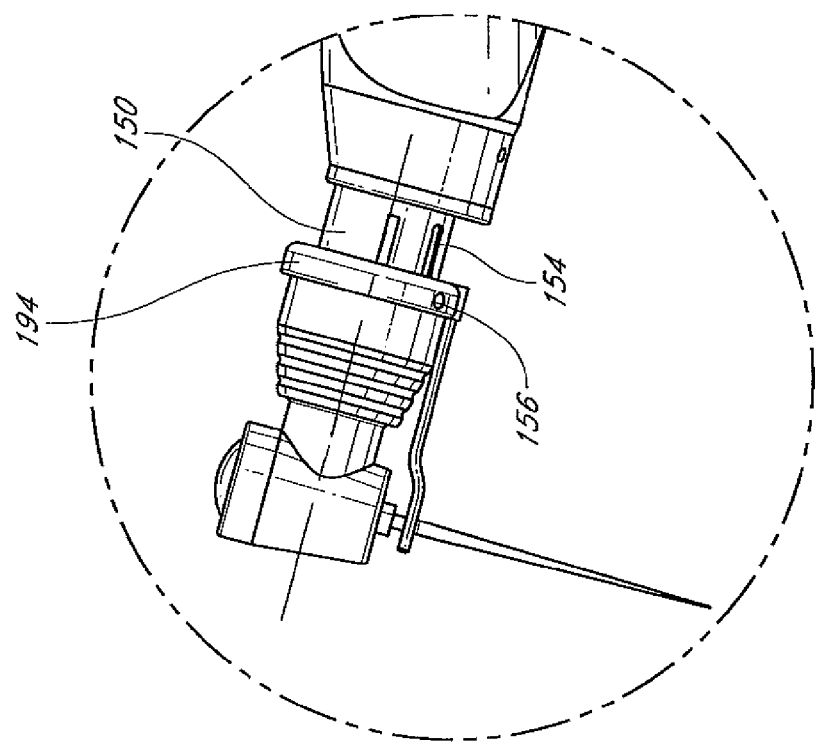
FIG. 8 is an enlarged view of a portion of the dental handpiece of FIG. 7, showing a movable contact collar in a first position.
Figure 10:
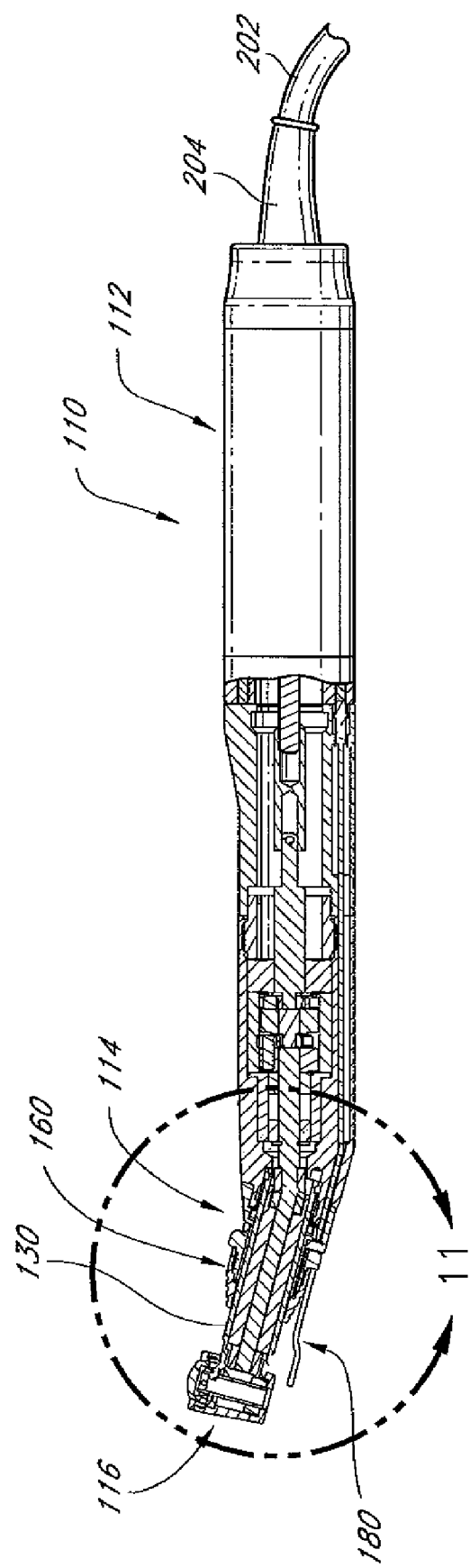
FIG. 10 is a partially sectioned cross-sectional view of the dental handpiece of FIG. 7.

A contact 40 is removably mounted to the collar 30 in any suitable manner. The contact 40 can have any suitable configuration. With reference now to FIG. 6, in the illustrated configuration, the contact 40 is generally U-shaped. The U-shape preferably has elongated legs 41 and a bight 43 (see FIG. 5) having a small radius. The elongated legs 41 preferably have a bent region 45 such that the legs converge together and then diverge again in a distal direction. Such a configuration is best shown in FIG. 6. The divergent portion allows the contact 40 to be easily slid onto and into contact with the dental instrument 38 such that the dental instrument 38 is secured between the legs 41 of the contact 40 and the legs 41 of the contact 40 can act as a brush to establish an electrical connection between the contact 40 and the rotating or stationary dental instrument 38.

With continued reference to FIG. 6, the contact 40 comprises a mounting block 42 in the illustrated arrangement. The legs 41 can be connected with or integrally formed with the mounting block 42 in any suitable manner and the mounting block 42 can have any suitable configuration. The mounting block 42 can be formed of an electrically conductive material in some advantageous embodiments.

In the illustrated arrangement, the mounting block 42 comprises tapering sidewalls 44 that correspond with the configuration of the slot walls 46 that define a docking region 48 in the collar 30. In this manner, the mounting block 42 can be securely slid into position within the collar 30 prior to being secured thereto by a fastener 52. The slot walls 46 and the sidewalls 44 need not be angled; however, the angled walls simplify the installation of the mounting block 42 into the docking region 48. In some configurations, for instance, the slot walls 46 may define a lower wall or a portion of a lower wall above which the mounting block 42 can be slid prior to being secured therein. Also, while the fastener 52 is used in the illustrated configuration, the contact 40 can be used using other suitable techniques, including but not limited to, cir-clips, pins, snap-fit constructions, interference fits and the like.

In some configurations, the contact 40 may be permanently mounted to the collar 30 such that repair or replacement of the contact 40 requires replacement or repair of the head unit 16. By providing the collar 30 with the docking region 48 and a removable mounting block 42, the illustrated arrangement provides a removable and replaceable contact 40 that allows operation of the dental handpiece 10 with or without the presence of the contact 40.

With reference again to FIG. 5, the collar 30 preferably comprises an outer housing 54 and an inner contact sleeve 56. The outer housing 54 preferably is formed of a suitable nonconductive material. Such materials are well known in the industry and are used to form a nonconductive barrier between the mouth and the handpiece 10 during use. In some configurations, a nonconductive coating can be used.

Figure 2:
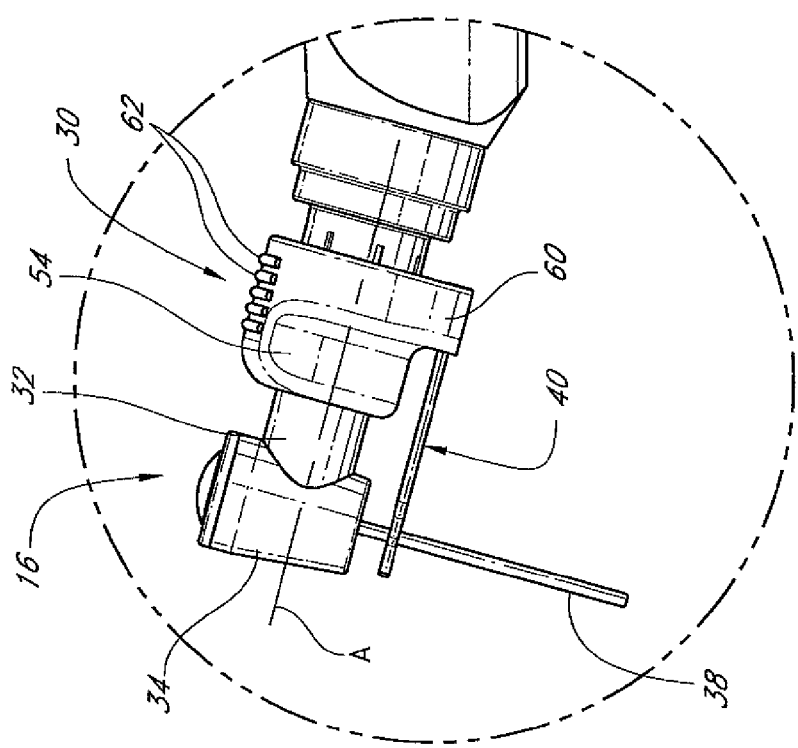
FIG. 2 is an enlarged view of a portion of the dental handpiece of FIG. 1, showing a movable contact collar in a first position.

With reference now to FIG. 2, the outer housing 54 preferably comprises a projecting portion 60 that accommodates the docking region 48 into which the mounting block 42 and the contact 40 can be secured. The outer housing 54 also preferably comprises a number of ridges 62 to provide increased traction between the collar 30 and a user's finger during movement of the collar 30 relative to the shank 32. In some configurations, the ridges 62 can be omitted while, in other configurations, other types of traction-improving structures can be used, including but not limited to, bumps, roughened surface regions and the like.

With reference to FIG. 5, the inner contact sleeve 56 preferably has a stepped configuration corresponding to an inner bore of the outer housing 54. The inner contact sleeve 56 in the illustrated arrangement advantageously has a larger diameter proximal end and a smaller diameter distal end. At least one aperture 70 extends through the inner contact sleeve 56. In the illustrated configuration, the aperture 70 is positioned at the step between the larger diameter portion and the smaller diameter portion.

The aperture 70 receives the fastener 52 and allows the illustrated mounting block 42 to be removably secured within the docking region 48 defined in the outer housing 54 of the collar 30 while advantageously providing an electrical connection between the inner contact sleeve 56 and the contact 40. Other types of connections can be used in which the fastener 52 is replaced by suitable interlocking structures, including but not limited clips, snaps, pins and the like.

A stepped transition member 72 preferably is mounted at a juncture between the neck section 14 and the head unit 16. The transition member 72 preferably is formed of a conductive material and is secured to the neck section 14 in any suitable manner. While the illustrated transition member 72 comprises three separate plateau regions, other suitable configurations also can be used keeping in mind the goal of providing an axially translatable collar 30 while maintaining an enlarged and substantially internalized signal circuit connection.

In the illustrated arrangement, a proximal end of the transition member 72 comprises a large diameter portion 74 that steps down to an intermediate portion 76. The intermediate portion 76 steps down to a small diameter portion 78. In the illustrated arrangement, an outer surface of the small diameter portion 78 is in sliding contact with an inner surface of the inner contact sleeve 56 and an outer surface of the intermediate diameter portion 76 of the stepped transition member 72 is in contact with an inner surface of another portion of the inner contact sleeve 56. Thus, suitable contact can be provided between the collar 30 and the stepped transition member 72. In some configurations, the transition member 72 and the collar 30 can be in electrical contact along one surface interface and, in other configurations, the transition member 72 and the collar 30 can be in electrical contact along more than two surface interfaces; however, in the illustrated configuration, the transition member 72 and the collar 30 are in electrical contact along two surface interfaces.

Preferably, the collar 30 is only capable of limited axial travel relative to the shank 32 such that the collar 30 cannot travel to such a degree that it is not inadvertently removed from the balance of the handpiece 10. Any suitable configuration can be provided for limiting the axial travel of the collar 30 relative to the shank 32. For instance, in some configurations, a slot and pin configuration can be used. In such a configuration, a pin can be positioned in one of the collar and the shank with a corresponding slot being positioned in the other of the two components. In one particular configuration, a slot is provided within the small diameter portion 78 of the stepped transition member 72 and a pin is secured in the collar 30 such that the pin protrudes into the slot defined within the small diameter portion 78. The pin restricts the axial travel of the collar to the range defined by the axial length of the slot. Any other suitable configuration, including the use of stops or the like, also can be used to provide a limited travel collar positioned on a shank of a dental handpiece head unit. While configurations can be used in which the collar 30 can be moved out of registry with the stepped transition member 72, a more secure connection between the collar 30 and the stepped transition member 72 can be provided by providing the collar 30 with limited travel.

The stepped transition member 72 further comprises an internal counter bore 80 that is defined at its proximal end. A ring 82 is positioned within the counter bore 80 and is in electrical contact therewith. In the illustrated arrangement, a conducting member 84 is secured to the ring 82 in any suitable manner. For instance, the conducting member 80 can be riveted into position relative to the stepped transition member 72 and the ring 82. In this manner, an electrical circuit can be defined from the conducting member 84 through the ring 82 and the stepped transition member 72, to the inner contact sleeve 56, through the fastener 52, and through the contact 40 to the cutting tool 38 such that the conducting member 84 is in electrical communication with the cutting tool 38.

Thus, the collar 30, which serves to secure the contact 40 to the dental handpiece 10, is connected to the conducting member 84. More preferably, the collar 30 is permanently connected to the conducting member 84, which is positioned within the handpiece (and in electrical communication with conductors within the cable 22, including through the case 20 of the main body 12). Such a configuration greatly decreases the likelihood, or even eliminates the likelihood, of the conducting member 84 having a faulty connection with the collar 30 and the contact 40 that is secured by the collar 30. Moreover, such a construction results in the contact 40 being positioned external to the head unit 16 and the corresponding shank 32. Such an external placement allows easy removable and replacement of the contact 40 from the collar 30 and the head unit 16 in general.

In use, the collar 30 can be slid in a proximal direction either before or after the contact 40 is assembled to the collar 30. In the illustrated construction, the mounting block 42 is slid into the recess defined by the docking region 48. Once inserted into the docking region 48, a fastener 52 can be used to secure the contact 40 in place relative to the illustrated collar 30. With the contact 40 assembled to the collar 30, the dental tool 38 can be inserted into the head unit 16. Once the dental tool 38 is coupled to the head unit 16, the collar 30 can be advanced distally such that the contact 40 is urged into electrical connection with the dental tool 38.

To remove the dental tool 38, the collar 30 is retracted in a proximal direction which removes the contact 40 from the dental tool 38. Once the dental tool 38 and the contact 40 are separated, the dental tool 38 can be removed from the head unit 16. With the dental tool 38 removed from the head unit 16, the contact 40 can be more easily removed from the handpiece 10. To remove the contact 40, the fastener 52 is loosened to a point that the mounting block 42 of the contact 40 can be slid distally out of the illustrated docking region 48.

With reference now to FIGS. 7 through 12, another handpiece 110 is illustrated that is arranged and configured in accordance with certain features, aspects and advantages of the present invention. The handpiece 110 is similar in most respects to the handpiece 10 described above. In the handpiece 110 illustrated in FIGS. 7 through 12, however, the electrode or contact element is mounted in a different manner than the contact 40 described above. In addition, while the outer housing 54 and the inner contact sleeve 56 are press fit together in the embodiment shown in FIGS. 1 through 6, the corresponding components in the embodiment shown in FIGS. 7 through 12 are preferably threaded together.

The dental handpiece 110 shown in FIGS. 7 through 12 generally can be constructed in the same manner as the dental handpiece 10 shown in FIGS. 1 through 6. For instance, the illustrated dental handpiece 110 generally comprises a main body 112, a neck section 114, and a head unit 116. The neck section 114 and the head unit 116 can be configured as an integrated unit or can be provided as separate components. When the components 114, 116 are provided separately, the components 114, 116 preferably are joined together in a suitable manner that will house the mechanical and electrical connections described herein or otherwise used to create a functional handpiece. In general, the neck section 114 and the main body 112 are separable to allow sterilization of the neck section 114 and the head unit 116 in manners known to those of ordinary skill in the art. Any suitable coupling can be used.

The illustrated main body 112 comprises a case 120 that defines an inner chamber (not shown). Within the inner chamber, the main body 112 preferably contains a drive motor (not shown). Any suitable drive motor can be used. In the preferred arrangement, the drive motor comprises an electric motor. In some configurations, an air motor or a pneumatic motor can be provided. Any other suitable drive motor also can be used. Rotation of an output shaft of the drive motor is conveyed to a cutting tool or other dental instrument using any suitable transmission mechanism.

The case 120 can be sized and configured to provide a suitable gripping area while keeping in mind the desire to encase the drive motor and the related transmission mechanism. In most embodiments, the gripping area is sized and configured for grasping by the hand of an operator during use of the handpiece 110. While pistol grip style constructions can be used, such constructions provide decreased operator control relative to the illustrated contra angle construction. Moreover, the gripping area can be formed at a forward location along the handpiece 110 such that the gripping area is generally adjacent or proximate to the head unit 116.

Figure 11:
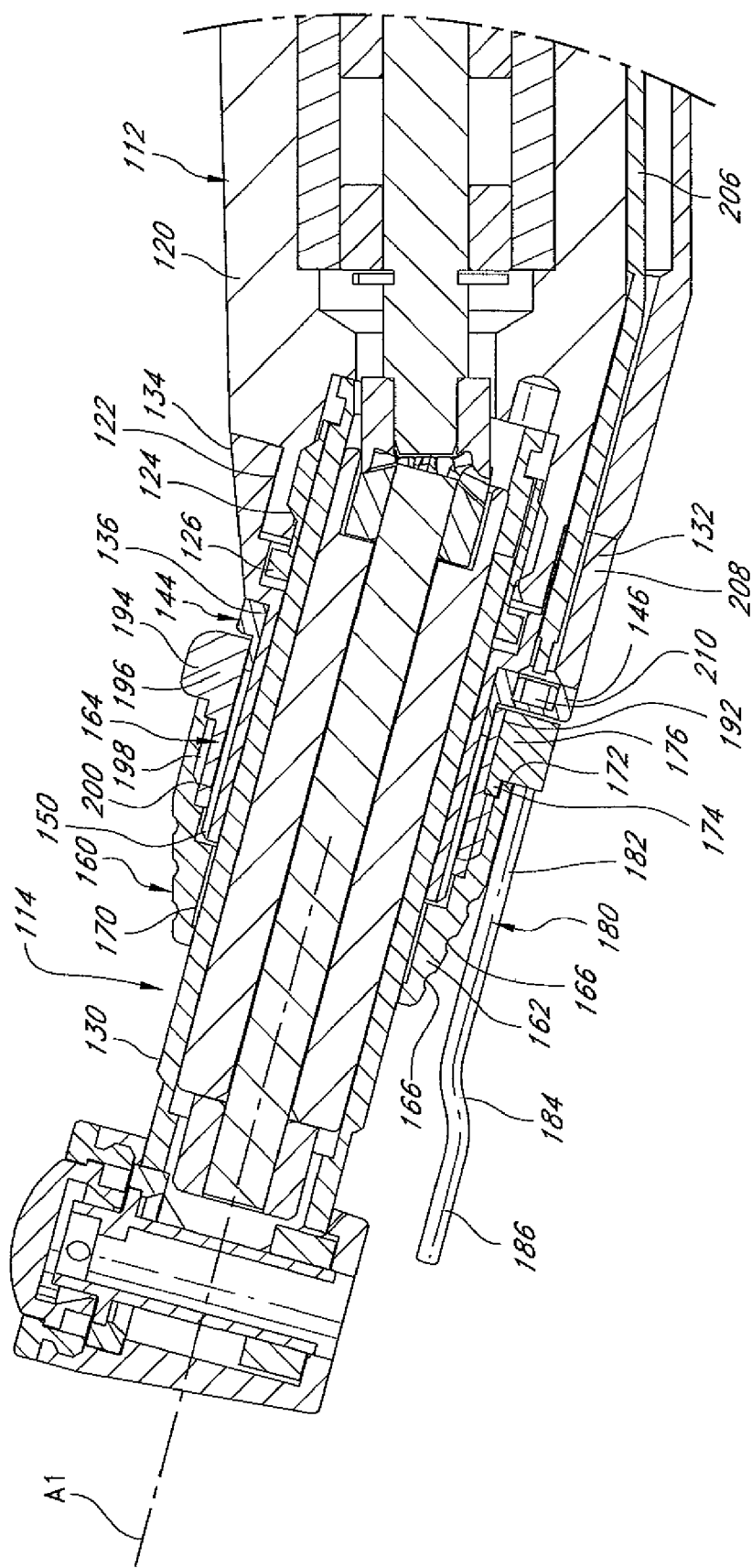
FIG. 11 is an enlarged view of the cross-section taken in FIG. 10 and showing an electrical connection between a contact and an internal circuit of the dental handpiece of FIG. 7.

A distal end of the case 120 comprises a mounting boss 122 (see FIG. 11). The mounting boss 122 preferably extends distally of the main portion of the case 120. The mounting boss 122 can have any suitable configuration. In the illustrated configuration, the mounting boss 122 is generally cylindrical. Preferably, an aperture 124 is defined through the mounting boss 122. More preferably, the aperture is internally threaded. Other configurations also can be used.

A sleeve 126 preferably extends inside of the aperture 124 of the mounting boss 122. The sleeve 126 more preferably comprises a threaded portion that is coupled to the internal threads of the aperture 124. Other techniques also can be used to join the sleeve 126 to the case 120 or to join the sleeve 126 to the mounting boss 122. For example but without limitation, the sleeve 126 and the boss can be pinned together or press fit together.

The illustrated sleeve 126 joins the neck section 114 to the main body 112. More particularly, the sleeve 126 preferably supports a portion of a shank 130 that extends into the mounting boss 122. The shank 130 and the sleeve 126 can be coupled together with a snap ring or the like that reduces the likelihood of the shank 130 from pulling out of the sleeve 126 in a distal direction. The shank 130 is generally fixed in location in the proximal direction because it generally abuts upon a wall of the case 120. Thus, the coupling between the sleeve 126 and the mounting boss 122 at least partially secures the shank 130 in position relative to the main body 112.

A transition member 132 extends from the case 120 toward the shank 130 in the illustrated configuration. Preferably, the transition member 132 encloses the mounting boss 122 and the sleeve 126. More preferably, the transition member 132 can comprise a contoured surface 134. The contoured surface 134 can be configured to conform to the shape of the case 120. In the illustrated configuration, the contoured surface 134 of the transition member 132 tapers toward the shank 130.

The illustrated transition member 132 also comprises a stepped region 136. In the illustrated embodiment, the stepped region 136 is generally cylindrical in configuration. The stepped region 136 advantageously extends along a portion of the shank 130 and provides additional support the shank 130 in some configurations. Other shapes other than cylindrical also can be used. Preferably, the inner shape of the stepped region 136 generally corresponds to the outer shape of the shank 130. Moreover, while the outer shape of the stepped region 136 also is generally cylindrical, other configurations can be used if desired. The illustrated configuration, however, is advantageously simple to construct and saves materials and machining costs.

The transition member 132 can be fixed to the case 120 in any suitable manner. In the illustrated configuration, the transition member 132 is pinned to the case 120. More particularly, in the illustrated configuration, the transition member 132 is pinned to the mounting boss 122. One, two or more pins 140 (see FIG. 12) can extend through corresponding openings 142 formed in the transition member 132. The pins 140 preferably are received within recesses or openings that are formed in a portion of the case 120. In one configuration, recesses are defined along the outer surface of the mounting boss 122. While the pins 140 have been shown and described, other configurations also can be used. For instance, the pins 140 could be set screws or other fastening components. In one configuration, a threaded coupling or an interlocking pin and slot (e.g., a stortz-type coupling) can be used.

A collar 144 preferably extends over at least a portion of the stepped region 136 of the transition member 132. The collar 144 in the illustrated configuration extends generally the same length along the shank 130 as the stepped region 136 of the transition member 132. Other lengths also can be used. The collar 144 generally comprises a flange 146 and a cylinder 150.

The flange 146 can be axially secured to the transition member 132 in any suitable manner. In the illustrated configuration, multiple threaded fasteners 152 join the two components 144, 132 together. In particular, the shank 130 defines a longitudinal axis A1 or other longitudinal datum line. In other words, the shank 132 need not be generally cylindrical in shape but can have other shapes, as desired. In some embodiments, the axis A1 may bend or be other than linear. The threaded fasteners 152 preferably extend generally parallel to at least a segment of the longitudinal axis A1. More preferably, the threaded fasteners 152 are countersunk into the flange 146 such that the heads of the fasteners 152 are generally flush with the distal surface of the flange 146 and, thus, the threaded fasteners 152 preferably extend generally normal to the flange 146. Other configurations are possible and the threaded fasteners 152 can be replaced by other suitable components, such as, for example but without limitation, mechanically interlocking components.

The cylinder 150 preferably comprises one or more slots 154. The slots 154 receive pins 156 that are connected to the axially translatable collar 160 in the illustrated embodiment. The slots 154 define limits to the amount of axial travel through which the collar 160 can move relative to the shank 130. In other words, the pins 156 are capable of sliding from one end to the other end of the slots 154 such that the ends of the slots 154 limit the axial travel of the pins 156. The pins 156, which are connected to the collar 160, limit the movement of the collar 160. Any other suitable configuration, including the use of stops or the like, also can be used to provide a limited travel collar positioned on a shank of a dental handpiece head unit. Preferably, the collar 160 is only capable of limited axial travel relative to the shank 130 such that the collar 160 cannot travel to such a degree that it is not inadvertently removed from the balance of the handpiece 110.

With reference again to FIG. 11, the illustrated collar 160 generally comprises an outer housing 162 and an inner contact sleeve 164. The collar 160 preferably is positioned on the shank 130. The collar 160 extends around the shank 130. While the illustrated collar 160 extends in a full circle, some constructions of the collar 160 may extend less than the full circle. Preferably, however, the illustrated collar 160 extends more than halfway around a full circle. Moreover, while described in the context of a circle, the collar 160 can be used with shanks having any desired configuration and, therefore, the collar 160 preferably encases the shank 130 regardless of its configuration. In some applications, the collar 160 extends around only a portion of the outer surface of the shank 130.

The collar 160, where the shank 130 is not generally cylindrical, preferably has a complementary shape and configuration. The collar 160 preferably is translatable in an axial direction relative to the datum line A1. In other words, the illustrated collar 160 defines a slideable member. In some other configurations, the collar 160 may rotate about the axis A1 rather than slide along the axis A1 or the collar 160 may slide along and rotate about the axis A1.

The outer housing 162 preferably is formed of a suitable nonconductive material. Such materials are well known in the industry and are used to form a nonconductive barrier between the mouth and the handpiece 110 during use. In some configurations, a nonconductive coating can be used.

In the illustrated configuration, the outer housing 162 comprises grooves 166 that enhance the ability of the operator to move the collar 160 in the axial direction. Any other suitable structure can be used to improve traction between a finger or fingers of the operator and the outer housing 162. In the illustrated construction, the outer housing 162 is grooved and tapered. In some configurations, other types of traction-improving structures can be used, including but not limited to, bumps, roughened surface regions and the like.

The outer housing 162 preferably has an inner bore 170 that has multiple steps. In one configuration, steps are provided to accommodate the shank 130, the cylinder 150 of the collar 144 and the inner contact sleeve 164. A lock step 172 also is provided in the illustrated outer housing 162 at its proximal end.

The lock step 172 is sized and configured to extend over a tab 174 of a mounting block 176 of a contact 180. The contact 180 is removably mounted to the collar 160 in any suitable manner. The contact 180 preferably comprises a pair of elongate legs 182. The legs 182 extend generally in parallel with each other in a direction generally parallel to the axis A1. The legs 182 can be integrally formed with the mounting block 176 or can be separately formed and attached to the mounting block 176. In the illustrated configuration, the legs 182 extend completely or substantially completely through the length of the mounting block. Preferably, the mounting block is formed of a conductive material.

The tab 174 preferably has a thickness that is less than the overall thickness of the mounting block 176. More preferably, the tab has a thickness that is less than the thickness of the mounting block 176 less the diameter of the legs 182 and less the thickness of the wall of the outer housing 162 that defines the lock step 172. In this manner, the wall that defines the lock step 172 can be received between the tab 174 and the legs 182. The illustrated tab 174 also comprises a rounded end wall. Other configurations also can be used; however, the rounded end wall eases insertion of the tab 144 into the appropriate position beneath the outer housing 162.

Figure 12:
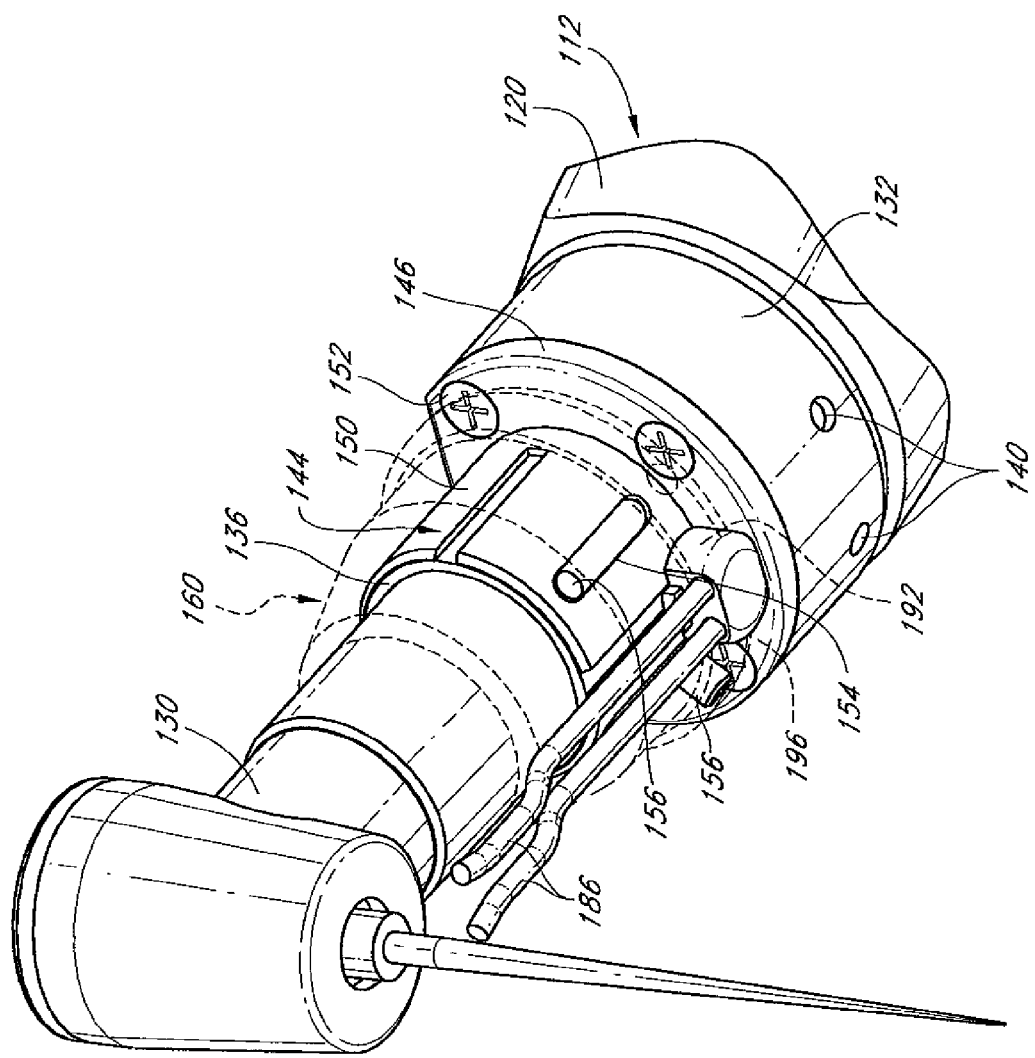
FIG. 12 is an enlarged perspective view of a portion of the dental handpiece of FIG. 7 in which a portion of the movable contact collar is shown in phantom line.

The legs 182 advantageously comprise an offset bend section 184 distal of the mounting block. The legs 182 preferably have a second bent region 186 such that the legs 182 converge together and then diverge again in a distal direction. Such a configuration is best shown in FIG. 12. The divergent portion allows the contact 180 to be easily slid onto and into contact with the dental instrument 190 such that the dental instrument 190 is secured between the legs 184 of the contact 180 and the legs 184 of the contact 180 can act as a brush to establish an electrical contact between the contact 180 and the dental instrument 190, whether the instrument 190 is stationary or rotating. The offset bend section 184 allows the legs 182 to extend closely along the outer housing 162 before moving down to a location along a dental instrument 190 that is further from the head unit 116. The dental instrument 190 can comprise a cutting tool, such as a file or reamer for example, or any other suitable dental instrument. The legs 182 can be assembled to the mounting block 176 in any suitable manner. In some configurations, the legs 182 are integrally formed with the mounting block. In other configurations, the legs 182 are separately formed and inserted into the mounting block 176.

The mounting block 176 is received within a recess 192 defined along an outer surface of the inner contact sleeve 164. The recess 192 preferably extends through a flange 196 of the inner contact sleeve 164. More preferably, the recess 192 extends through the flange 196 until the recess 192 in the flange 196 is generally flush with a base 200 of the inner contact sleeve 164. Thus, the flange 196 can be interrupted by the recess 192. In the illustrated configuration, the mounting block 176 and the recess 192 comprise complementary curved lateral surfaces such that the mounting block 176 can be more securely positioned in the recess 192.

The inner contact sleeve 164 can be removably joined to the outer housing 162 in any suitable manner. In a preferred configuration, the inner contact sleeve 164 and the outer housing 162 are threaded together at a threaded coupling 198. In the illustrated arrangement, the threaded coupling 198 is positioned along a smaller diameter distal end of the inner contact sleeve 164 and a corresponding portion of the outer housing 162. Thus, the mounting block 176 can be positioned within the recess 192 prior to the outer housing 162 being tightened onto the inner contact sleeve 164. As the outer housing 162 is tightened onto the inner contact sleeve 164, the lock step captures the tab 174 of the mounting block 176 and the mounting block 176 is thereby secured to the collar 160. Advantageously, the mounting block 176 is thereby secured to the base 200 of the inner contact sleeve 164. Thus, the outer housing 162 can be loosened on the inner contact sleeve 164 at the threaded coupling 198 such that the mounting block 176 of the contact 180 can be inserted into and removed from the recess 192 defined in the inner contact sleeve 164.

As explained above, in some configurations, the contact 180 may be permanently mounted to the collar 160 such that repair or replacement of the contact 180 requires replacement or repair of the head unit 116. The illustrated arrangement, however, provides a removable and replaceable contact 180 that allows operation of the dental handpiece 110 with or without the presence of the contact 140. The illustrated arrangement also allows the contact 180 to be easily replaced without replacement of the head unit 116.

The drive motor is supplied with electricity and/or control signals via suitable electrical conductors. In the illustrated arrangement, the electrical conductors are contained with a cable 202. The cable 202 extends into the proximal end of the illustrated main body 112. In the illustrated arrangement, a flexible boot 204 enshrouds the end of the cable 202 and provides protection to the coupling between the cable 202 and the main body 112. While the illustrated embodiment is shown in the context of a handpiece having a cable 202, certain features, aspects and advantages of the present invention may find utility with other types of handpieces, including cordless handpieces, for instance, but without limitation.

An electrical conductor 206 is routed through the main body 112 in any suitable manner. Preferably, a passage 208 is defined through the transition member 132 and into the flange 146 of the collar 144. An electrical terminal 210 can be mounted in a recess formed in the collar 144. Other suitable configurations also can be used.

In the illustrated configuration, an electrical path is defined from the electrical conductor 206 to the electric terminal 210, from the electric terminal 210 through the collar 144, from the collar to the inner contact sleeve 164, from the inner contact sleeve 164 to the mounting block 176, from the mounting block 176 to the legs 182, and from the legs 182 to the dental instrument 190. The inner contact sleeve 164 is adapted to translate along the cylinder 150 of the collar 144. Thus, an elongated contact interface is defined between the collar 160 and the collar 144.

The collar 160, which serves to secure the contact 180 to the dental handpiece 110, is connected to the electrical conductor 206. More preferably, the collar 160 is permanently connected to the electrical conductor 206, which is positioned within the handpiece 110 (and in electrical communication with conductors within the cable 202, including through the case 120 of the main body 112). Such a configuration greatly decreases the likelihood, or even eliminates the likelihood, of the conducting member 202 having a faulty connection with the collar 160 and the contact 180 that is secured by the collar 160. Moreover, such a construction results in the contact 180 being positioned external to the head unit 116 and the corresponding shank 130. Such an external placement allows easy removable and replacement of the contact 180 from the collar 160 and the head unit 116 in general.

In use, the collar 160 can be slid in a proximal direction either before or after the contact 180 is assembled to the collar 160. In the illustrated construction, the mounting block 176 is slid into the recess 192 defined in the inner contact sleeve 164. Once inserted into the recess 192, the outer housing 162 can be tightened onto the inner contact sleeve 164 via the threaded coupling 196. Tightening the two components 162, 164 together captures at least a portion of the contact 180. With the contact 180 assembled to the collar 160, the dental instrument 190 can be inserted into the head unit 116. Once the dental instrument 190 is coupled to the head unit 116, the collar 160 can be advanced distally such that the contact 180 is urged into electrical connection with the dental instrument 190.

To remove the dental instrument 190, the collar 160 is retracted in a proximal direction which removes the contact 180 from the dental instrument 190. Once the dental instrument 190 and the contact 180 are separated, the dental instrument 190 can be removed from the head unit 116. With the dental instrument 190 removed from the head unit 116, the contact 180 can be more easily removed from the handpiece 110. To remove the contact 180, the outer housing 162 is loosened from the inner contact sleeve 164 to a point that the mounting block 176 of the contact 180 can be removed from the recess 192.

Although the present invention has been described in terms of a certain embodiment, other embodiments apparent to those of ordinary skill in the art also are within the scope of this invention. Thus, various changes and modifications may be made without departing from the spirit and scope of the invention. For instance, various components may be repositioned as desired. Moreover, not all of the features, aspects and advantages are necessarily required to practice the present invention. Accordingly, the scope of the present invention is intended to be defined only by the claims that follow.

What is claimed is:

1. A dental handpiece and collar construction comprising a main body, a neck section and a head unit, a cable extending into a proximal end of said main body, a distal end of said main body being connectable to said neck section, said head unit comprising a shank, said shank comprising a longitudinal axis, said collar being positioned around said shank and being moveable along said longitudinal axis, said collar comprising an outer housing and an electrically conductive inner sleeve, said inner sleeve being in electrical communication with a conducting member that extends through said neck section of said dental handpiece, said outer housing comprising a projecting portion, a docking region defined within said projecting portion, said docking region comprising a wall, a mounting block positionable within said docking region, said mounting block comprising a wall that abuts with said wall of said docking region, a contact secured to said mounting block such that said contact is positioned external of said head unit, said contact comprising a generally U-shaped configuration, and said inner sleeve being in electrical communication with said contact.

2. The dental handpiece and collar construction of claim 1, wherein said inner sleeve has a stepped configuration, said head unit comprises a stepped transition member and said inner sleeve abuts said stepped transition member.

3. The dental handpiece and collar construction of claim 2, wherein said stepped configuration of said inner sleeve comprises two cylindrical portions, with a proximal cylindrical portion being a larger inner diameter of said two cylindrical portions, both said proximal portion and said distal portion abutting said stepped transition member.

4. The dental handpiece and collar construction of claim 2, wherein said stepped transition member comprises three cylindrical portions, said proximal cylindrical portion being a largest outer diameter of said three cylindrical portions, said distal cylindrical portion being a smallest outer diameter of said three cylindrical portions, and an intermediate cylindrical portion abutting said inner sleeve.

5. The dental handpiece and collar construction of claim 4, wherein said distal cylindrical portion also abuts said inner sleeve.

6. The dental handpiece and collar construction of claim 1, wherein said sleeve is slideable relative to said shank portion.

7. A dental handpiece and collar construction comprising a handpiece, a conducting member extending internally through said handpiece, said handpiece comprising a head unit, said head unit comprising a shank, said shank comprising a longitudinal axis and an outer surface, a collar positioned over said outer surface of said shank and being slideable along said longitudinal axis, a contact secured to said collar and said contact being positioned vertically below said head unit, said contact being in electrical communication with said conducting member via an electrically conductive portion of said collar, and said contact abutting a cutting tool positioned in said handpiece when said collar is slid axially along said shank toward said cutting tool.

8. The dental handpiece and collar construction of claim 7 further comprising a transition member that is positioned between said collar and said conducting member, said transition member comprising a portion of an electrical connection between said contact and said conducting member.

9. The dental handpiece and collar construction of claim 8, wherein said collar abuts said transition member in at least one location.

10. The dental handpiece and collar construction of claim 9, wherein a generally cylindrical portion of said collar abuts a generally cylindrical portion of said transition member.

11. The dental handpiece and collar construction of claim 10, wherein said contact is removable from said collar.

12. The dental handpiece and collar construction of claim 11, wherein said contact comprises a mounting block and said collar comprises a docking portion, said mounting block being received within said docking portion.

13. The dental handpiece and collar construction of claim 12, wherein said docking portion comprises a pair of angled walls such that said mounting block is secured in said collar by said angled walls.

14. The dental handpiece and collar construction of claim 13, wherein said mounting block is further secured in said docking portion by a fastener.

15. The dental handpiece and collar construction of claim 14, wherein said fastener places said contact in electrical communication with said collar.

16. A dental handpiece and collar construction comprising a head unit, said head unit comprising a shank and a head housing, said head housing being connected to a main body, said shank extending in a proximal direction from said head housing and comprising a longitudinal axis, a sleeve positioned within said head housing, said sleeve adapted to retain a cutting tool for use with said dental handpiece, a collar positioned about said shank of said head unit and moveable along the longitudinal axis of said shank, a contact removably connected to said collar, said contact adapted to contact the cutting tool when said sleeve is moved along said longitudinal axis in a distal direction, and said contact being in electrical communication with an electrical path that extends between said collar and said main body through an internal portion of said head unit.

17. The dental handpiece and collar construction of claim 16, wherein said collar comprises an inner sleeve and said contact is in electrical communication with said inner sleeve.

18. The dental handpiece and collar construction of claim 17, wherein a fastener forms an electrical path between said inner sleeve and said contact.

19. The dental handpiece and collar construction of claim 18, wherein said head unit further comprises a transition member and said inner sleeve abuts said transition member in at least one location.

20. The dental handpiece and collar construction of claim 19, wherein said inner sleeve and said transition member are abutting along a generally cylindrical interface.

* * * * *